US00PP12243P2

(12) United States Plant Patent
Matsukizono

(10) Patent No.: US PP12,243 P2
(45) Date of Patent: Dec. 4, 2001

(54) PORTULACA PLANT NAMED 'SUMMER JOY DEEP ROSE'

(75) Inventor: Hiromi Matsukizono, Irisa (JP)

(73) Assignee: Sakata Corporation, Yokohama (JP)

( * ) Notice: Subject to any disclaimer, the term of this patent is extended or adjusted under 35 U.S.C. 154(b) by 0 days.

(21) Appl. No.: 09/353,041

(22) Filed: Jul. 13, 1999

(51) Int. Cl.[7] ..... A01H 5/00
(52) U.S. Cl. ..... Plt./263
(58) Field of Search ..... Plt./263

(56) References Cited

U.S. PATENT DOCUMENTS

P.P. 11,349 * 4/2000 Babikow ..... Plt./263

OTHER PUBLICATIONS

UPOV ROM GTITM Computer Database 2000/04, GTI JOUVE Retrieval Software, citation for 'Summer Joy Deep Rose', Aug. 2000.*

* cited by examiner

*Primary Examiner*—Bruce R. Campell
*Assistant Examiner*—Wendy Baker
(74) *Attorney, Agent, or Firm*—Rothwell, Figg, Ernst & Manbeck

(57) ABSTRACT

Portulaca 'Summer Joy Deep Rose' is a new variety of *Portulaca oleracea*. This plant has a vigorous, spreading plant growth which produces large, dark pink flowers having a red center.

1 Drawing Sheet

BACKGROUND OF THE NEW PLANT

This invention relates to a new and distinct cultivar of Portulaca plant, hereinafter referred to by the name 'Summer Joy Deep Rose'. Portulaca 'Summer Joy Deep Rose' is a new variety of *Portulaca oleracea*. The plant has a vigorous spreading growth habit and can be used as a ground cover. It can also be used in a potted or hanging basket presentation. The invention's flowers are dark pink (RHS 74A) with a red (RHS 46A) center. The flowers are single and measure 5.4 to 5.8 centimeters in diameter when fully open. There are five distinct petals with an indent at the tip of each petal. Portulaca flowers will typically close under low light and low temperature conditions such as late in the day and at night. 'Summer Joy Deep Rose' Portulaca flowers will stay open later into the evening than most other cultivated varieties. The plant performs well in hot and dry climates. The plant is very resistant to rain, heat and drought.

ORIGIN AND ASEXUAL REPRODUCTION

The new cultivar is propagated asexually from vegetative cuttings. The asexual reproduction establishes that the plant does in fact maintain the characteristics described in successive generations. 'Summer Joy Deep Rose' has been reproduced by stem cuttings in Salinas, Calif., and all of the characteristics thereof have been determined to be firmly fixed.

'Summer Joy Deep Rose' originated from a hybridization made by the inventor Hiromi Matsukizono in Japan. The female parent is a commercial variety known as 'Yubi® Rose', an unpatented variety of Portulaca and the male parent was a commercial variety known as 'Yubi® Apricot'. The initial cross-pollination of the parents, resulting in $F_1$generation seed, was made in June, 1992. In February, 1993, the $F_1$seed was sown. From these plants, five plants were selected for appealing flower color. In June through September of 1993 the five selected plant lines were vegetatively propagated and tested for easy reproducibility and stability of traits. One of these five plant lines was hence selected for dark pink flower color, large flower size and easy propagation. In February, 1997, cuttings of this plant line were sent to California. During the spring and summer of 1997 and 1998, plants were grown under the direction and supervision of the inventor for evaluation of the stability of the line's desired traits. Plants were evaluated in greenhouse pots at the research station at Salinas, Calif., and at the breeding station in Kakegawa, Japan. The invention, 'Summer Joy Deep Rose' Portulaca, was determined by the inventor to have its characteristics, as herein described, firmly fixed.

BRIEF DESCRIPTION OF DRAWINGS

The accompanying drawings serve by color photographic means to illustrate the new plant variety, 'Summer Joy Deep Rose'. The colors are represented as true as possible using conventional photographic procedures.

DETAILED DESCRIPTION OF THE NEW VARIETY

Figure 1:
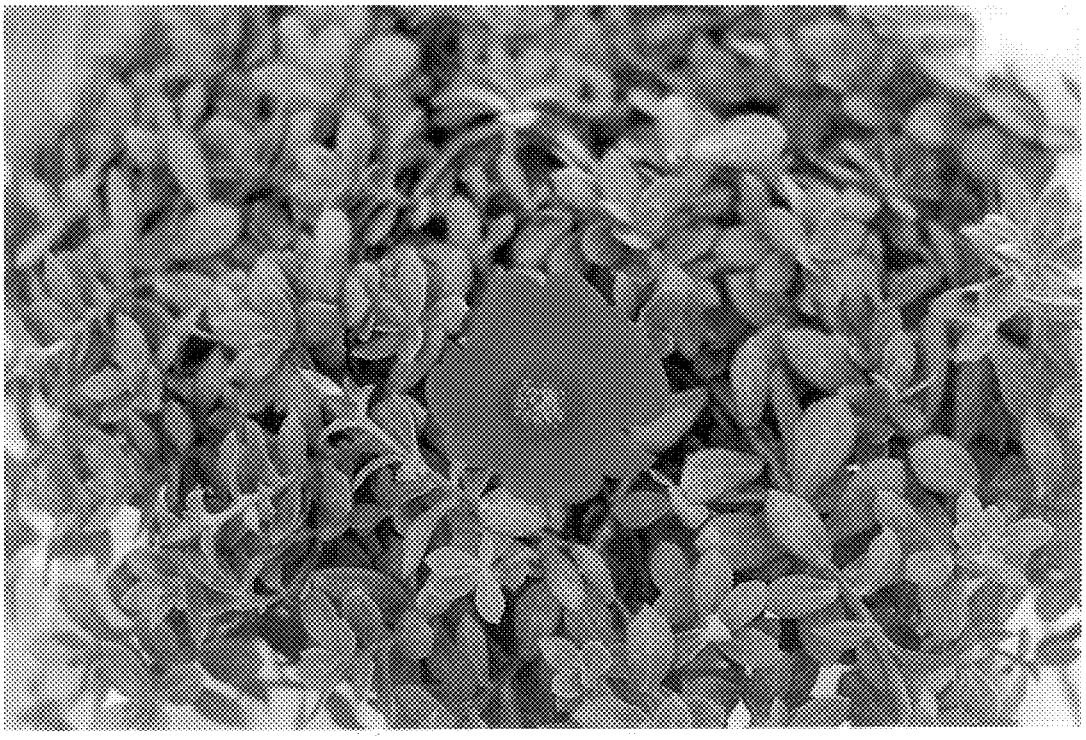
FIG. 1 is a close-up view of a 'Summer Joy Deep Rose' flower illustrating its color and shape.
Figure 2:
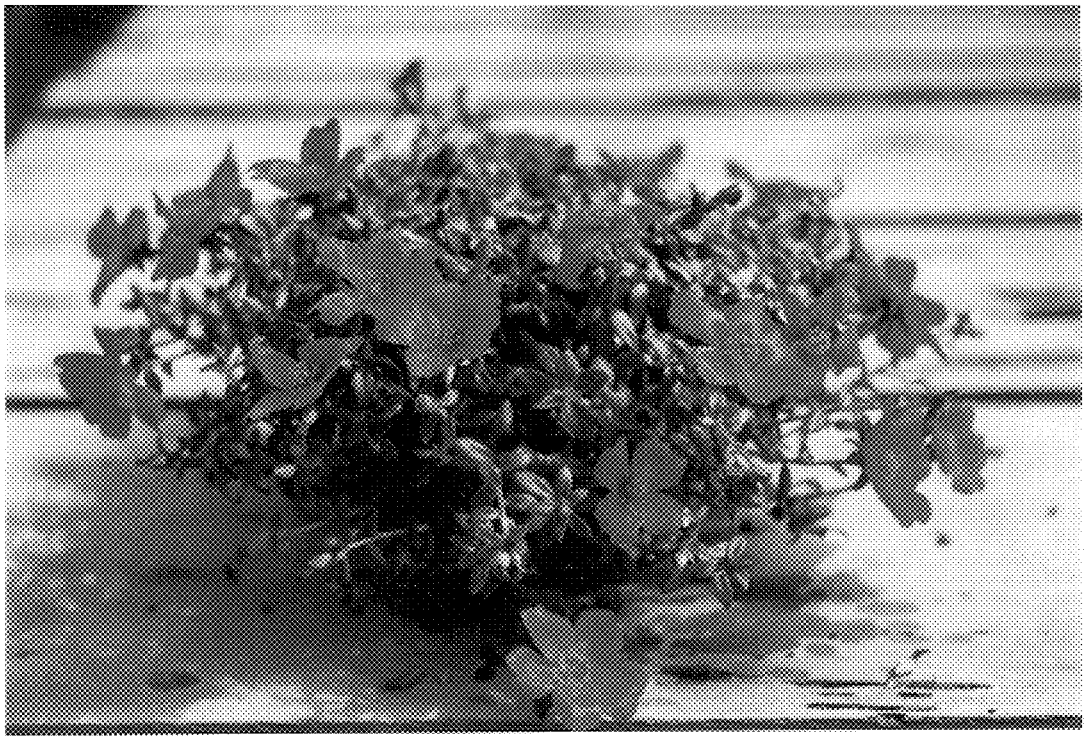
FIG. 2 is a view of the new cultivar after growing in a greenhouse for 8 to 10 weeks in a six-inch diameter pot.

The following description is based on observations and measurements from 14–16 week old plants grown in six-inch pots at Salinas, Calif. These plants were grown in plastic pots containing a peat moss-based medium. The plants were grown in the greenhouse under full sunlight in Salinas, Calif. Night temperatures ranged from 16° C. to 21° C. and day temperatures ranged from 24° C. to 35° C. The soil was not allowed to stay saturated but the plants were irrigated when the soil began to dry, or every second or third day. Soluble fertilizer was applied through an overhead irrigation system. The fertilizer contained 18% nitrogen, 8% phosphorus and 18% potassium. Every fourth irrigation was done with non-fertilizer water. Color designations were made according to The Royal Horticultural Society Colour Chart published by The Royal Horticultural Society of London, England.

Origin: Japan.

Parentage:

*Female parent.*—Yubi® Rose (not patented).

*Male parent.*—Yubi® Apricot (not patented).

Classification:

*Family.*—Portulacaceae.

*Genus.*—Portulaca.

*Species.*—Oleracea.

*Commercial.*—Portulaca/Purslane 'Summer Joy Deep Rose'.

Plant:

*Growth Habit.*—Prostrate.

*Plant height.*—7 cm.

*Spreading area of plant.*—60–80 cm (in a six-inch pot).

*Vigor.*—The plant is most vigorous at high temperatures.

*Time to initiate/develop roots.*—Vegetative cuttings root in 7–10 days after placing into a rooting medium such as a peat moss-based mixture. The cuttings will form roots without the use of overhead mist.

Stem:

*Thickness.*—2.3 mm.

*Color.*—Yellowish green (144C) with red-purple RHS 60A anthocyanin pigment present in the axial portion of the stem.

*Pubescence.*—None.

*Branching.*—Abundant.

*Length of internode.*—5–15 mm.

Leaf:

*Shape.*—Oblanceolate with cuspidate tip.

*Length* (*average*).—2.4 cm.

*Width* (*average*).—1.1 cm.

*Petiole.*—Contains anthocyanin pigment (red purple RHS 63B).

*Thickness.*—1.2 mm.

*Color.*—Upper leaf surface is green RHS 137A and the lower surface is green (137C) with red-purple (60A) anthocyanin present at the edge.

*Pubescence.*—None.

*Texture.*—Leaf surface is smooth, shiny and wax-like. Leaves are thick and fleshy.

Flower:

*Shape.*—Five distinct petals with an indent at tip of petal.

*Petal shape.*—Heart-shaped with a square; approximately 2.0×1.8 cm.

*Lobation.*—None.

*Diameter.*—5.4–5.8 cm when fully opened.

*Color.*—Unopened stage (the development stage at which the petals have elongated from the sepals but not yet fully extended and opened): Dark pink (74B); Upper petal color is red-purple (74A); Lower petal color is red-purple (74B). Mature stage: Upper petals are red-purple (74A) with a deep red (46A) center; Lower petals are red-purple (74B).

*Bud.*—Lanceolate shaped; mature bud measures 1.6 cm in length and 0.7 cm in diameter; color is yellow-green (145A).

*Sepal.*—Two sepals, deltoid shaped; measures 1 cm in length and 0.9 cm in width; sepals are thin, paper-like, smooth and shiny; color is transparent with green venation.

*Habit.*—The flowers bloom during midmorning and close at night. Each flower blooms only once and are produced throughout the growing season. The plants produce flowers regardless of day length; the plants are day neutral. Plants can have 40 to 50 open flowers at one time and have no fragrance.

*Season of bloom.*—In zone 9 and similar locations this plant will flower throughout the entire year. Growth is less vigorous during the cool temperatures and short days of winter, but the plant will continue to bloom.

*Hardiness.*—Plant is heat tolerant; thrives in heat and humidity; plant is not cold tolerant or below 7° C.

*Reproductive organs.*—One pink (53A) pistil with five narrow style branches and many stamen with orange-yellow (17B) anthers and red filaments; does not produce seed.

Disease and Insect Resistance

No unusual susceptibility to diseases or insects have been observed.

Comparison with Other Known Varieties

The new variety is distinguished from other Portulaca plants known to inventor by its flower color, larger flower size and ability to stay open later into the evening. The closest commercial cultivar that we are aware of is the Portulaca plant named 'Yubi® Rose' (an unpatented variety). The distinguishing characteristics, which differentiate 'Summer Joy Deep Rose' from 'Yubi® Rose', are:

| | 'Summer Joy Deep Rose' | 'Yubi ® Rose' |
|---|---|---|
| Flower Diameter | 5.4–5.8 cm | 4.2–4.7 cm |
| Flower Color | Dark pink with a red center | Reddish purple with a yellow center |
| Flower Closing Behavior | Open longer in evening | Closes earlier in afternoon |

We claim:

1. A new and distinct cultivar of Portulaca as shown and described herein.

* * * * *